(12) United States Patent
Mirjafari

(10) Patent No.: US 11,434,520 B2
(45) Date of Patent: Sep. 6, 2022

(54) LONG-TERM DNA PRESERVATION AND STORAGE AT AMBIENT TEMPERATURE

(71) Applicant: Florida Gulf Coast University Board of Trustees, Fort Myers, FL (US)

(72) Inventor: Arsalan Mirjafari, Bonita Springs, FL (US)

(73) Assignee: Florida Gulf Coast University Board of Trustees, Fort Meyers, FL (US)

( * ) Notice: Subject to any disclaimer, the term of this patent is extended or adjusted under 35 U.S.C. 154(b) by 481 days.

(21) Appl. No.: 16/519,810

(22) Filed: Jul. 23, 2019

(65) Prior Publication Data

US 2020/0080131 A1 Mar. 12, 2020

Related U.S. Application Data

(60) Provisional application No. 62/729,175, filed on Sep. 10, 2018.

(51) Int. Cl.
*C12Q 1/68* (2018.01)
*C12Q 1/6806* (2018.01)
*C12Q 1/6844* (2018.01)
*C12Q 1/6848* (2018.01)

(52) U.S. Cl.
CPC ......... *C12Q 1/6806* (2013.01); *C12Q 1/6844* (2013.01); *C12Q 1/6848* (2013.01); *C12Q 2523/10* (2013.01)

(58) Field of Classification Search
CPC . C12Q 1/6806; C12Q 2523/10; C12Q 1/6848
See application file for complete search history.

(56) References Cited

U.S. PATENT DOCUMENTS

2014/0030719 A1 1/2014 Kwon et al.
2015/0335547 A1 11/2015 Patel et al.

OTHER PUBLICATIONS

Baust, et al., "Strategies for the Storage of DNA," Biopreservation and Biobanking, Dec. 2008, vol. 6, No. 4, Mary Ann Liebert, Inc., Bethesda, Maryland.
Bonnet et al., "Chain and conformation stability of solid-state DNA: implications for room temperature storage," Nucleic Acids Research, 2010, vol. 38(5), p. 1531-1546, Oxford University Press.
Chandran, et al., "Groove binding mechanism of ionic liquids: a key factor in long-term stability of DNA in hydrated ionic liquids?" Journal of the American Chemical Society, Nov. 2012, vol. 134;50, p. 20330-20339, American Chemical Society.
Hammouda, et al., "The Denaturation Transition of DNA in Mixed Solvents," Biophysical Journal, Sep. 2006, vol. 91, p. 2237-2242, the Biophysical Society.
Jobling, et al., "Encoded Evidence: DNA in Forensic Analysis," Nature Reviews Genetics, Oct. 2004, vol. 5, p. 739-751, Springer Nature Publishing AG.
Kutzler et al., "DNA vaccines: ready for prime time?" Nature Reviews Genetics, Oct. 2008, vol. 9(10), p. 776-788, Nature Publishing Group.
Legoff et al., "Influence of storage temperature on the stability of HIV-1 RNA and HSV-2 DNA in cervicovaginal secretions collected by vaginal washing," Journal of Virological Methods, Dec. 2006, vol. 138(1-2), p. 196-200, Elsevier B.V.
Lukin et al., "NMR Structures of Damaged DNA," Chemical Reviews, Feb. 2006, vol. 106(2), p. 607-686, American Chemical Society Publications.
Mirjafari et al., "Building a bridge between aprotic and protic ionic liquids," RSC Advances, Nov. 2012, vol. 3 (2), p. 337-340, Royal Society of Chemistry Publishing.
Nakano et al., "Choline Ion Interactions with DNA Atoms Explain Unique Stabilization of A—T Base Pairs in DNA Duplexes: A Microscopic View," The Journal of Physical Chemistry, 2014, vol. 118, p. 379-389, American Chemical Society.
Reilly et al., "Study of biocatalytic activity of histidine ammonia lyase in protic," Journal of Molecular Liquids, Dec. 2017, vol. 248, p. 830-832.
Singh et al., "Very High Concentration Solubility and Long-Term Stability of DNA in an Ammonium-Based Ionic Liquid: A Suitable Medium for Nucleic Acid Packaging and Preservation," ACS Sustainable Chemical Engineering, Jan. 2017, vol. 5, p. 1998-2005, American Chemical Society Publications.
Unknown, "DNA Casework Technical Procedures," California Department of Justice Bureau of Forensic Services, Apr. 23, 2018, vol. 1, Document No. TP-6, p. 1-802.
Vijayaraghavan et al., "Long-Term Structural and Chemical Stability of DNA in Hydrated Ionic Liquids," The Journal of the German Chemical Society, Feb. 2010, vol. 49, p. 1631-1633, WILEY-VCH Verlag GmbH & Co. KGaA, Weinheim.
International Search Report and Written Opinion dated Jan. 2, 2020 for International Patent Application No. PCT/US2019/043003.
Invitation to Pay Additional Fees dated Oct. 29, 2019 for International Patent Application No. PCT/US2019/043003.
International Preliminary Report on Patentability dated Mar. 25, 2021, issued in International Application No. PCT/US2019/043003.

*Primary Examiner* — Jezia Riley

(74) *Attorney, Agent, or Firm* — Rouget F. Henschel; Potomac Law Group, PLLC

(57) ABSTRACT

Aprotic-protic ionic salt (APS) compositions and methods of using aprotic-protic ionic salt compositions to stabilize nucleic acids at ambient temperatures are provided. Certain aspects provide aprotic-protic ionic salt compositions for long term storage of nucleic acids at ambient temperature in the presence of aqueous solvents.

4 Claims, 13 Drawing Sheets

LONG-TERM DNA PRESERVATION AND STORAGE AT AMBIENT TEMPERATURE

All references cited herein, including, but not limited to patents and patent applications, are incorporated by reference in their entirety.

CROSS-REFERENCE TO RELATED APPLICATIONS

This application claims the benefit of U.S. Provisional Patent Application No. 62/729,175 filed Sep. 10, 2018, which is hereby incorporated by reference in its entirety.

BACKGROUND

Deoxyribonucleic acid (DNA) is a naturally-occurring biopolymer, which has been recognized as a key component in genomics, biotechnology, pharmaceutical, environmental and forensic sciences as well as (nano)materials to develop advanced molecular devices (Jobling & Gill, 2004; Kutzler at al., 2008) and recently, direct-to-consumer (DTC) genetic testing (such as 23andMe). Naturally-occurring typical consists of four nucleic acid bases, adenine (A), guanine (G), cytosine (C), and thymidine (T) arranged in a double-stranded, helical molecule.

In coding regions of DNA, the base pairs form three letter codes for one of twenty amino acids. The amino acids can be assembled into proteins the cell during protein synthesis using ribonucleic acid (RNA) as an intermediary. DNA typically resides in the cell nucleus and is duplicated during cell division and heritable during sexual reproduction. The four base pairs (A, T, C, G) are arranged into double-stranded helical molecules when A pairs with T and C pairs with G on opposite strands through hydrogen bonding.

Regions of DNA molecules (e.g., genes, genetic markers) encode one or more proteins which impart a trait (e.g., susceptibility to disease) or can be used to uniquely identify an individual, determine paternity or maternity, etc., by identifying mutations (e.g., single-nucleotide polymorphisms) associated with an individual or group. The sequence of nucleotides in DNA and other nucleic acids can be determined by obtaining biological material from a subject (e.g., blood, hair, skin, and bodily fluids), isolating the nucleic acid by known methods, and sequencing the nucleic acid by a variety of methods. The genetic markers identified by sequencing the DNA have a variety of applications.

In particular, DNA can be used in forensics when biological material is associated with a crime or other legal case. Identification of victims of wars, disasters and accidents are greatly facilitated by DNA preserving/banking methods. Degradation of DNA has a key impact on the results generating errors that are both quantitative and qualitative on downstream applications such as PCR-based and hybridization assays. Thus, there is a need for compositions and methods for long-term storage of DNA. While DNA can be frozen and stored for long periods, such methods require specialized equipment that may not be readily available in the field or at a crime scene.

Despite these needs, long-term stability of DNA in aqueous media at ambient conditions is challenging. The stability of the DNA double helix depends on a balance of interactions including hydrogen bonds between nucleotide bases, hydrogen bonds between bases and surrounding water molecules, and base-stacking interactions between adjacent bases.

Although DNA is considered a relatively stable macromolecule in aqueous solution, it is susceptible to hydrolysis, depurination and deamination, which can cause damage to DNA structure (Lukin & de los Santos, 2006), In addition, various conditions (i.e., temperature, pH, ionic strength and solvent properties) can disrupt the DNA helix, leading to denaturation—unwinding of the ordered helical structure into the two single-stranded constituents (Baust, 2008).

DNA stability was investigated in a variety of non-aqueous solvents (Hammouda & Worcester 2006). DNA loses its duplex stability when dissolved in dimethyl sulfoxide (DMSO), dimethyl formamide (DMF) or methanol (MeOH), while it is retained in ethylene glycol. Id. However, DNA molecules are not stable in solution at room temperatures for long periods (more than a month). Commonly, DNA samples are stored in cryogens for long-term storage (between −80° C. and −164° C.) (Legoff et al., 2006), which costs labs worldwide ~USD 30 billion per year.

Alternatively, dry storage of nucleic acids by exploiting the principles of anhydrobiosis, can be used in place conventional cold storage of DNA (Bonnet et al., 2010). However, the major drawback of this method is if moisture is added to the 'dry state' or the temperature is raised above the glass transition temperature of water, damage to the DNA can occur. Therefore, finding the efficient and cost-effective preserving media to dissolve DNA and preserve it for long periods of use at room temperature is an important goal.

Ionic liquids (ILs) are salts composed of cations such as imidazolium ions, pyridinium ions and anions such as $BF_4^-$, $PF_6^-$ and are liquid below 100° C. Their characteristic properties include; (1) close to zero vapor pressure, (2) non-flammability, (3) high thermal stability, (4) liquid state over extended temperature ranges, (5) high ionic conductivity. ILs have been used for the dissolution of a number naturally-occurring biopolymers such as cellulose and DNA (Brandt et al., 2013; Shamshina et al. 2019) Recently, biocompatible choline-based ionic liquids were explored for the long-term preservation and storage of DNA (Vijayaraghavan et al., 2010; Sing et al., 2017). The electrostatic interaction between choline and the DNA phosphate backbone is strong, accompanied by hydrophobic and polar interactions between ionic liquids and DNA major and minor grooves. Also, anions form hydrogen bonds with cytosine, adenine and guanine bases.

However, use of choline-based salts have poor thermal stability limiting their use for DNA preservation and for direct polymerase chain reaction (PCR) amplification. DNA loss can occur at both the DNA extraction and quantification steps, which is not ideal, especially for forensic evidence containing low levels of DNA. Direct PCR amplification of has been suggested to circumvent extraction and quantification, thereby retaining the DNA typically lost during those procedures.

While ILs containing protic and aprotic domains can stabilize enzymes such as histidase (Reilly et al., 2017), these ILs have not been shown to stabilize nucleic acids. In addition, the enzyme was better stabilized by chaotropic $NTf_2^-$ anion compared to the enzyme with lesser chaotropic $Cl^-$ anions (Reilly et al., 2017) making these ILs less desirable for stabilizing nucleic acids. In addition, $NTf_2^-$ salts are more toxic and expensive relative to $Cl^-$ salts.

SUMMARY OF THE INVENTION

In one aspect, compositions and methods of concentration, dissolution, and stable storage of nucleic acids (e.g., DNA, RNA) in dicationic salts for long-term storage at ambient temperature while maintaining structural integrity of the nucleic acids are provided. In another aspect, salts (e.g., aprotic-protic salts (APSs) and aprotic-protic ionic liquids (APILs)) with linked protic and aprotic centers can be used in place of previously used choline-based ionic liquids and dry DNA storage for the preservation of DNA (e.g. DNAstable® Plus). As described herein, exemplary APSs have been synthesized, and structurally and thermophysical characterized.

In another aspect, stability of DNA molecules (e.g., human kidney tissue DNA) dissolved in the APSs was maintained for at least two years at ambient (e.g., room) temperature. In a further aspect, these salts utilize dications in which the protic center of a BrØnsted acid-base pair is fixed into a non-volatile state by a covalent tether to an aprotic cationic center.

Further aspects provide APSs comprising a compound selected from the group consisting of:

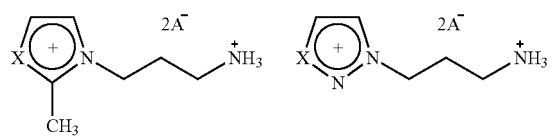

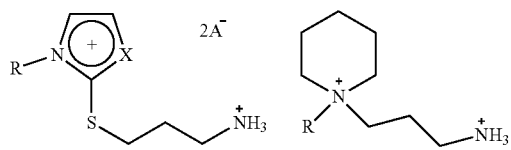

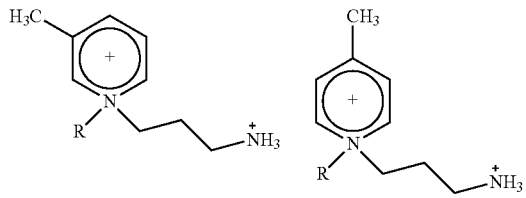

wherein X is N, O, or S; wherein A is Cl, Br, I, OTf, NTf$_2$, BF4, PF6, OAc, N(CN)$_2$, MeSO$_3$, H$_2$PO$_3$, dialkylphosphate, SCN, citrate, docusate, bis(oxylate)borate, oxalate, alaninate, or serinate; and wherein R is CH$_3$—C$_{16}$H$_{37}$, pyroether groups, C—O—C, CH$_3$—C$_{20}$H$_{41}$, CH$_3$OCH$_2$, CH$_3$OCH$_2$CH$_2$, CH$_3$CH$_2$OCH$_2$CH$_2$OCH$_2$CH$_2$, or CH$_3$CH$_2$OCH$_2$CH$_2$OCH$_2$CH$_2$OCH$_2$CH$_2$.

In one aspect, the APSs comprise:

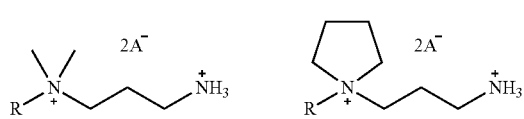

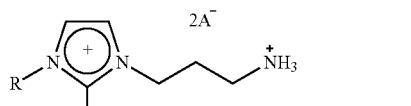

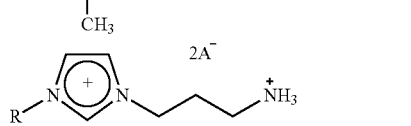

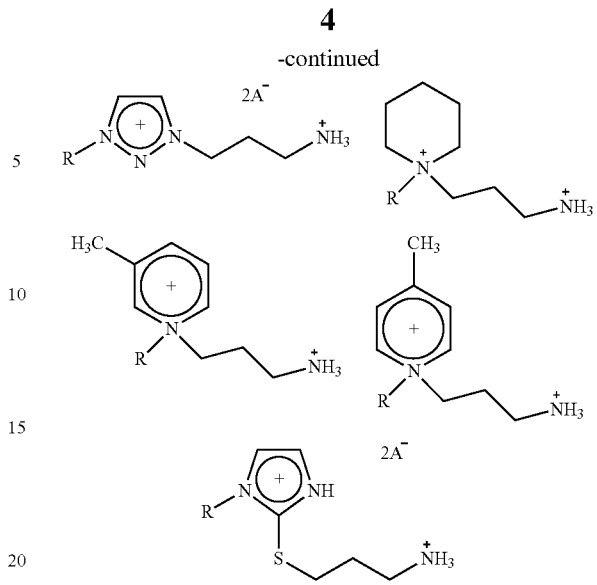

In yet another aspect, aprotic-protic salts are provided in a composition comprising a compound selected from the group consisting of:

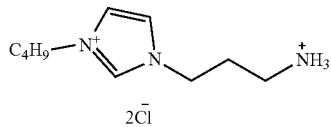
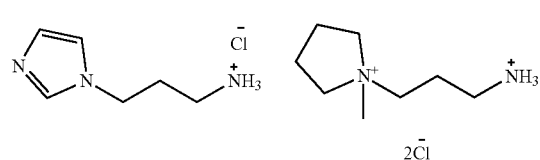

and a solvent (e.g., water (e.g., deionized water), ethanol, and a phosphate buffer solution or any other suitable solvent).

One aspect provides an aprotic-protic ionic salt composition comprising a compound selected from the group consisting of:

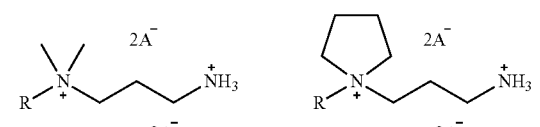

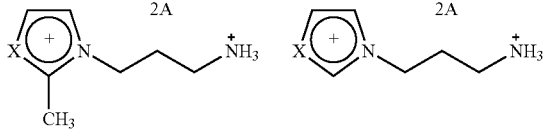

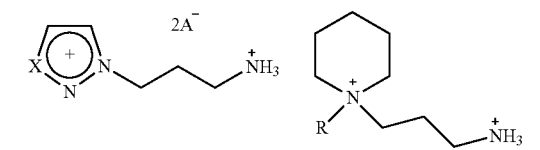

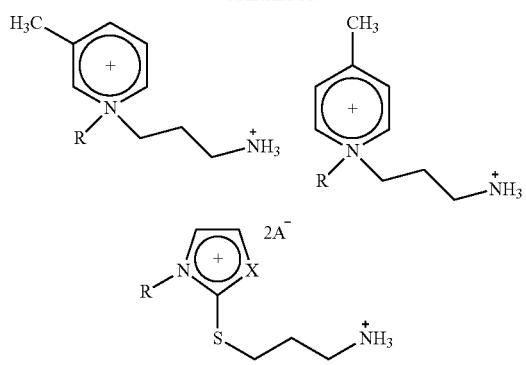

wherein X is N, O, or S; wherein A is Cl, Br, I, OTf, NTf$_2$, BF$_4$, PF$_6$, OAc, N(CN)$_2$, MeSO$_3$, H$_2$PO$_3$, dialkylphosphate, SCN, citrate, docusate, bis(oxylate)borate, oxalate, alaninate, or serinate; and wherein R is CH$_3$—C$_{16}$H$_{37}$, pyroether groups, C—O—C, CH$_3$—C$_{20}$H$_{41}$, CH$_3$OCH$_2$, CH$_3$OCH$_2$CH$_2$, CH$_3$CH$_2$OCH$_2$CH$_2$OCH$_2$CH$_2$, or CH$_3$CH$_2$OCH$_2$CH$_2$OCH$_2$CH$_2$OCH$_2$CH$_2$; a solvent, and a nucleic acid mixture.

Further aspects provide an aprotic-protic salt composition comprising a compound selected from the group consisting of:

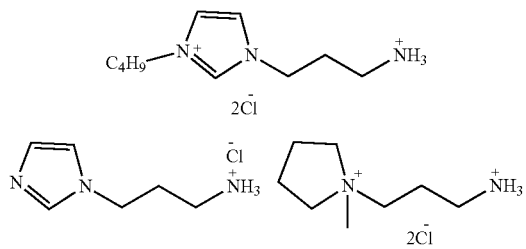

a solvent, and a nucleic acid mixture.

Aspects described herein provide methods of stabilizing the structure of nucleic acid comprising dissolving a nucleic acid mixture in a solution comprising a compound selected from the group consisting of:

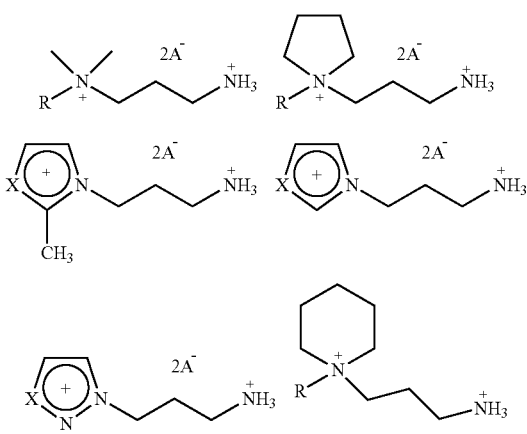

wherein X is N, O, or S; A is Cl, Br, I, OTf, NTf$_2$, BF$_4$, PF$_6$, OAc, N(CN)$_2$, MeSO$_3$, H$_2$PO$_3$, dialkylphosphate, SCN, citrate, docusate, bis(oxylate)borate, oxalate, alaninate, or serinate; R is CH$_3$—C$_{16}$H$_{37}$, pyroether groups, C—O—C, CH$_3$—C$_{20}$H$_{41}$, CH$_3$OCH$_2$, CH$_3$OCH$_2$CH$_2$, CH$_3$CH$_2$OCH$_2$CH$_2$OCH$_2$CH$_2$, or CH$_3$CH$_2$OCH$_2$CH$_2$OCH$_2$CH$_2$OCH$_2$CH$_2$; and a solvent (e.g., water, ethanol, and a phosphate buffer solution).

Further aspects provide a kit comprising a compound selected from the group consisting of:

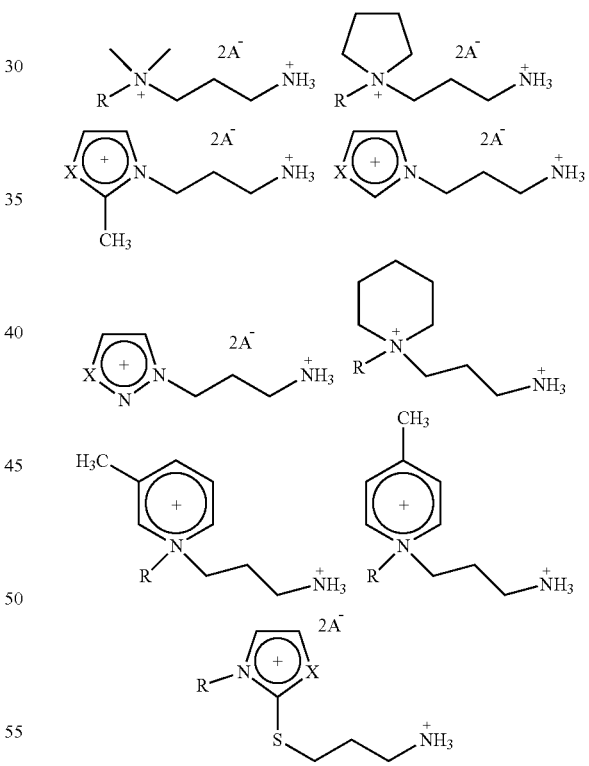

wherein X is N, O, or S; A is Cl, Br, I, OTf, NTf$_2$, BF$_4$, PF$_6$, OAc, N(CN)$_2$, MeSO$_3$, H$_2$PO$_3$, dialkylphosphate, SCN, citrate, docusate, bis(oxylate)borate, oxalate, alaninate, or serinate; R is CH$_3$—C$_{16}$H$_{37}$, CH$_3$—C$_{16}$H$_{37}$, CH$_3$—C$_{16}$H$_{37}$, pyroether groups, C—O—C, CH$_3$—C$_{20}$H$_{41}$, CH$_3$OCH$_2$, CH$_3$OCH$_2$CH$_2$, CH$_3$CH$_2$OCH$_2$CH$_2$OCH$_2$CH$_2$, or CH$_3$CH$_2$OCH$_2$CH$_2$OCH$_2$CH$_2$OCH$_2$CH$_2$; and a solvent (e.g., water, ethanol, and a phosphate buffer solution).

Further aspects provide methods of amplifying nucleic acid by obtaining a nucleic acid mixture sample; dissolving the nucleic acid mixture sample in the compounds described herein and a solvent; and amplifying nucleic acid from the nucleic acid mixture using one or more nucleic acid probes wherein the DR of the nucleic acid mixture sample is at least about 1 for at least about 30 days.

The dicationic materials described herein can reduce or eliminate the need for cryogens and freezers, permitting storage of the nucleic molecules at ambient lab temperatures in the presence of water. In addition, storage at room temperature permits the use of direct PCR or other nucleic acid amplification methods without the need for additional steps (e.g., DNA extraction, purification, or quantification). DNA-APS system directly to an amplification process without being subjected to prior DNA extraction, purification or quantification.

DETAILED DESCRIPTION

As described herein, storage of genomic DNA in synthesized salts (APSs) preserves DNA integrity from at least 30 days to at least two years at ambient temperature and in the presence of water. Without being bound by theory, it is believed that DNA integrity can be preserved for five years or longer. Genomic DNA storage in the APSs described herein can reduce or eliminate the need for refrigeration or freezing to preserve DNA integrity—even in the presence of aqueous solutions (e.g., water).

Figure 1:
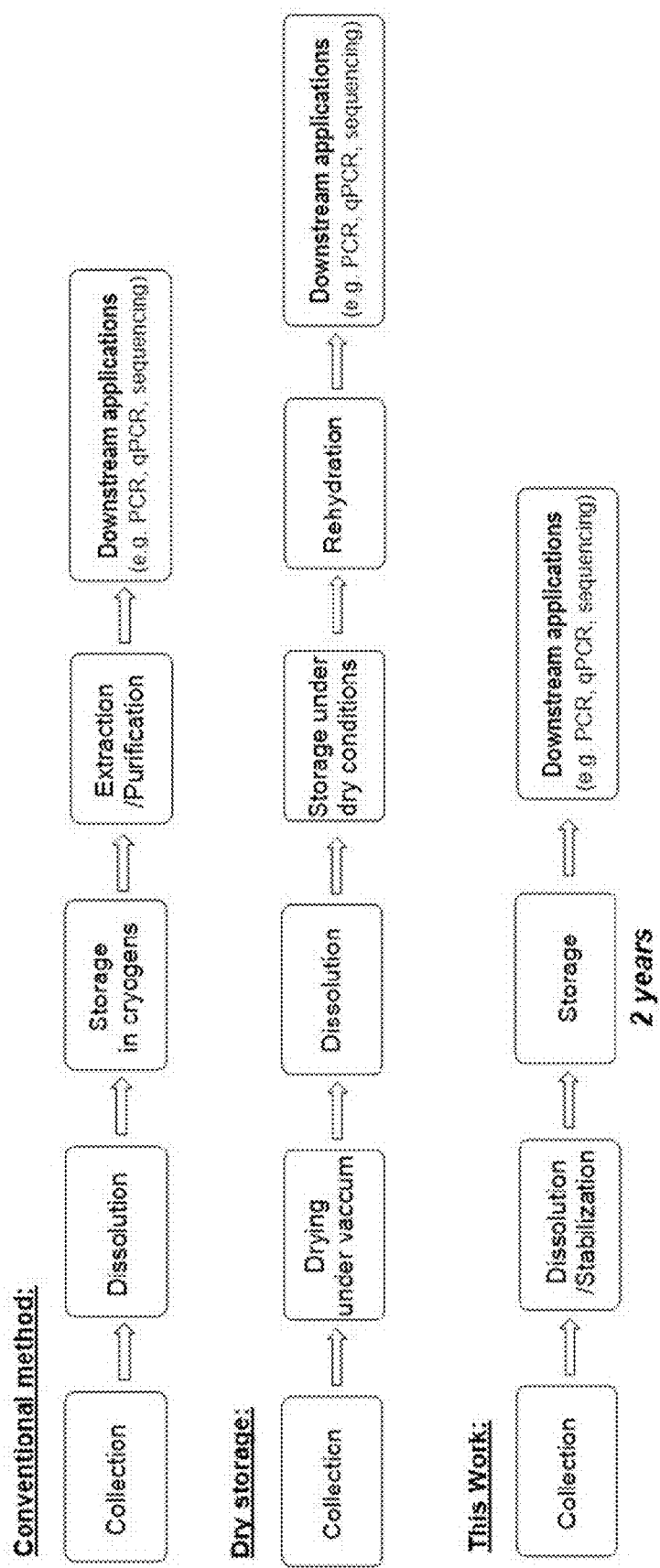
FIG. 1 illustrates an exemplary process for DNA stabilization methods and exemplary methods of using aprotic-protic salts as described herein.
Figure 2:
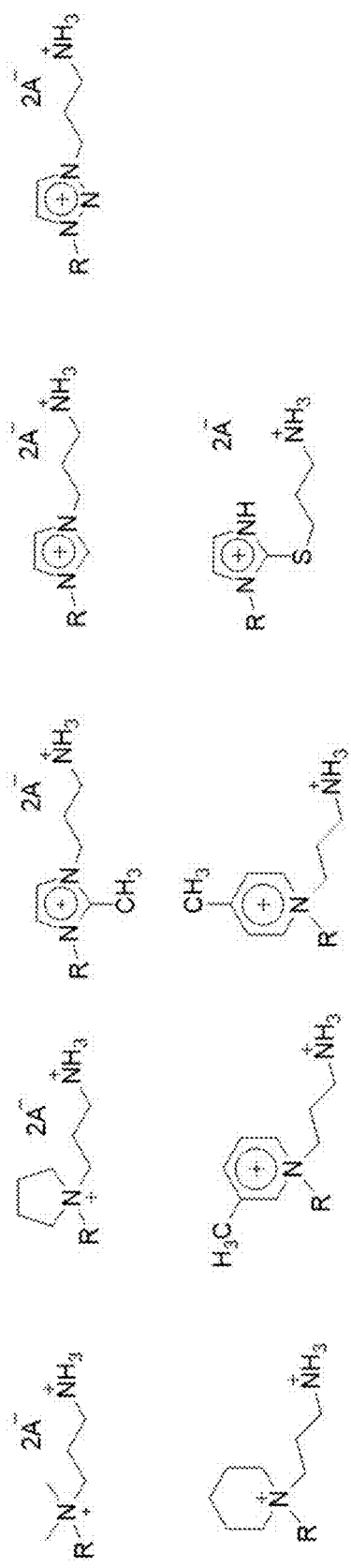
FIG. 2 provides exemplary structures of aprotic-protic salts as described herein.

The advantages of an exemplary process utilizing the hydrophobic solvent materials are summarized in FIG. 1. Aspects described herein provide a class of novel media/solvents to dissolve nucleic acids (DNA, RNA) and preserve the nucleic acids for a long time at ambient temperature without requiring dry conditions (liquid format). Further aspects described herein provide a nucleic acid-containing solution for direct downstream analysis such as PCR, real-time PCR (qPCR) or sequencing. In this aspect, exemplary aprotic-protic salts (APSs) were synthesized (FIG. 2). This exemplary synthesis methodology can be applied to access a large library of molecules as new media for DNA preservation and storage. Furthermore, the R (FIG. 2) moiety can be linear and branched alkyl chains, of varying lengths, can be employed. Table 1 below provides the degradation ratio (DR) for exemplary DNA preserved in selected APSs as described herein.

TABLE 1

Degradation ratio (DR) of selected APSs on DNA stability as measured by real-time PCR

| APSs | Structure | Degradation Ratio | Standard deviation |
|---|---|---|---|
| 1 | pyrrolidinium-propyl-NH$_3^+$, 2NTf$_2^-$ | 1.325 | 0.09 |
| 2 | pyrrolidinium-propyl-NH$_3^+$, 2Cl$^-$ | 0.8235 | 0.02 |
| 4 | imidazolium (C$_4$H$_9$)-propyl-NH$_3^+$, 2NTf$_2^-$ | 0.9545 | 0.1 |
| 5 | pyrrolidinium-propyl-NHMe$_2^+$, 2NTf$_2^-$ | 1.75 | 0.7 |
| 10 | imidazolium-propyl-NH$_3^+$, 2NTf$_2^-$ | 1.25 | 0.11 |

TABLE 1-continued

Degradation ratio (DR) of selected APSs on DNA stability as measured by real-time PCR

| APSs | Structure | Degradation Ratio | Standard deviation |
|---|---|---|---|
| 36 | 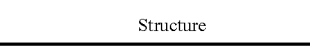 | 0.89 | 0.16 |

Aspects described herein provide aprotic-protic salts comprising a compound selected from the group consisting of:

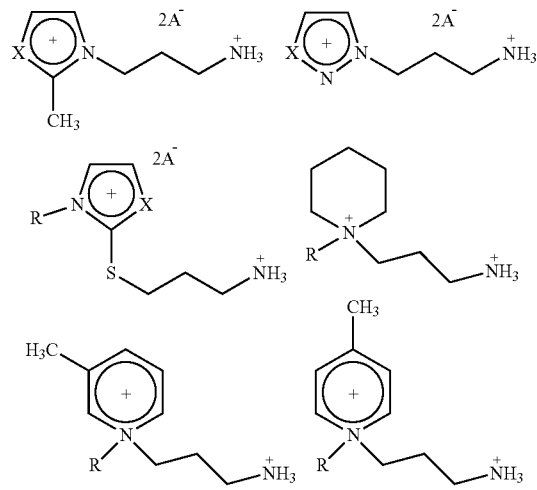

wherein X is N, O, or S; wherein A is Cl, Br, I, OTf, $NTf_2$, $BF_4$, $PF_6$, OAc, $N(CN)_2$, $MeSO_3$, $H_2PO_3$, dialkylphosphate, SCN, citrate, docusate, bis(oxylate)borate, oxalate, alaninate, or serinate; and wherein R is $CH_3$—$C_{16}H_{37}$, pyroether groups, C—O—C, $CH_3$—$C_{20}H_{41}$, $CH_3OCH_2$, $CH_3OCH_2CH_2$, $CH_3CH_2OCH_2CH_2OCH_2CH_2$, or $CH_3CH_2OCH_2CH_2OCH_2CH_2OCH_2CH_2$.

The term "aprotic-protic salt" refers to dicationic salts in which one charge center is protic and the other is aprotic. In one aspect, the protic center of a BrØnsted acid-base pair is linked to a non-volatile state by a covalent tether to an aprotic cationic center. Aprotic-protic salts can include aprotic-protic ionic liquids. The aprotic-protic salt can further comprise a solvent (e.g., water (e.g., deionized water), ethanol, and a phosphate buffer solution or any other suitable solvent). The aprotic-protic salt can, for example, be dissolved in the solvent before or after addition of nucleic acid as described herein.

In one aspect, X is N. In another aspect, A is $NTf_2$.

In a further aspect, the aprotic-protic salts are provided in a composition comprising a compound selected from the group consisting of:

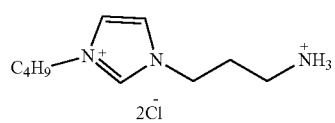

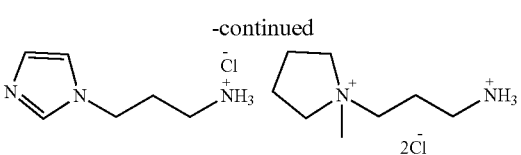

and a solvent (e.g., water (e.g., deionized water), ethanol, and a phosphate buffer solution or any other suitable solvent).

In yet another aspect, the aprotic-protic ionic salt composition comprises a compound selected from the group consisting of:

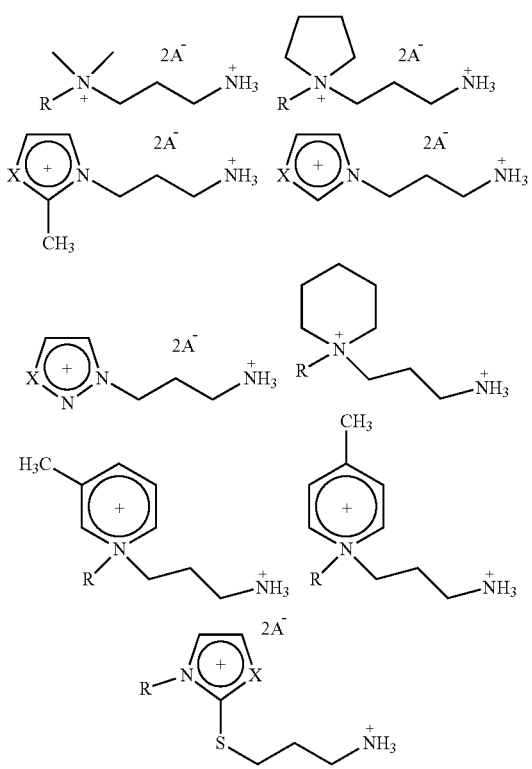

wherein X is N, O, or S; wherein A is Cl, Br, I, OTf, $NTf_2$, $BF_4$, $PF_6$, OAc, $N(CN)_2$, $MeSO_3$, $H_2PO_3$, dialkylphosphate, SCN, citrate, docusate, bis(oxylate)borate, oxalate, alaninate, or serinate; and wherein R is $CH_3$—$C_{16}H_{37}$, pyroether groups, C—O—C, $CH_3$—$C_{20}H_{41}$, $CH_3OCH_2$, $CH_3OCH_2CH_2$, $CH_3CH_2OCH_2CH_2OCH_2CH_2$, or $CH_3CH_2OCH_2CH_2OCH_2CH_2OCH_2CH_2$; a solvent, and a nucleic acid mixture.

The term "nucleic acid mixture" refers to a sample of material that contains or is suspected of containing nucleic acid (e.g., tissue sample, bodily fluid, cell scraping etc.). The sample of material can be collected, for example, by medical or health personnel from a patient in a doctor's office, clinic, diagnostic testing facility and the like for purposes of conducting diagnostic tests.

The sample of material can be obtained directly from a subject, living or dead, or obtained from scene of suspected criminal activity. The sample may be obtained by a variety of forensic methods and transferred to a kit containing components of aspects described herein in order to preserve material.

The sample of material can also be experimental material obtained from laboratory experiments including from cell culture or animal subjects or polymerase chain reaction experiments. The sample of material may be obtained by the subject from a cell scraping, for example, placed in the components of aspects described herein and sent to a laboratory for further testing.

In a further aspect, the solvent can be selected from the group consisting of water, ethanol (EtOH), dimethyl sulfoxide (DMSO) and a phosphate buffer solution. Any suitable solvent can be used to obtain a desired outcome. For example, solvents suitable or necessary to conduct a particular diagnostic test can be used in aspects described herein.

Any nucleic acid (e.g., double-stranded, single-stranded, non-natural base, etc.) can be utilized in aspects described herein. In one aspect, the nucleic acid can be selected from the group consisting of DNA, RNA, and miRNA.

Further aspects provide an aprotic-protic salt composition comprising a compound selected from the group consisting of:

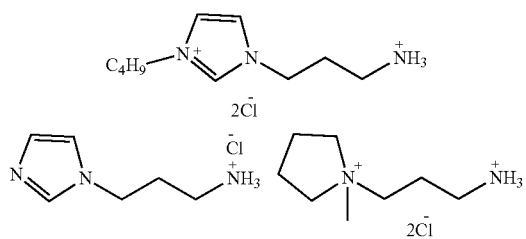

a solvent, and a nucleic acid mixture.

In this aspect the solvent can selected from the group consisting of water, ethanol, DMSO, and a phosphate buffer solution. In a further aspect, the nucleic acid can be selected from the group consisting of DNA, RNA, and miRNA.

Aspects described herein provide methods of stabilizing the structure of nucleic acid comprising dissolving a nucleic acid mixture in a solution comprising a compound selected from the group consisting of:

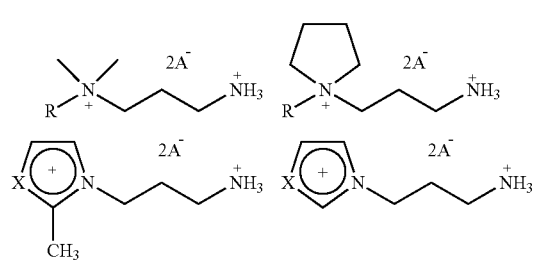

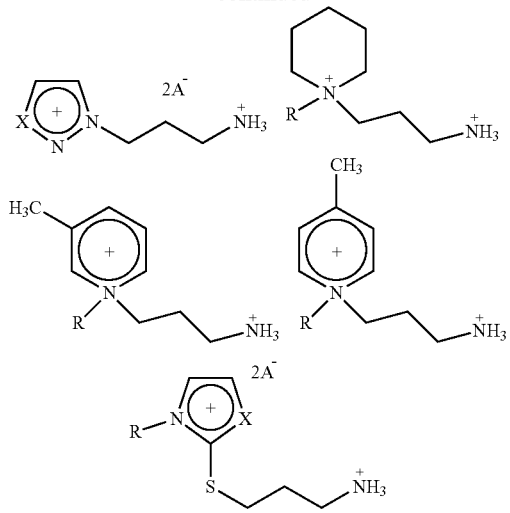

wherein X is N, O, or S; A is Cl, Br, I, OTf, $NTf_2$, $BF_4$, $PF_6$, OAc, $N(CN)_2$, $MeSO_3$, $H_2PO_3$, dialkylphosphate, SCN, citrate, docusate, bis(oxylate)borate, oxalate, alaninate, or serinate; R is $CH_3$—$C_{16}H_{37}$, pyroether groups, C—O—C, $CH_3$—$C_{20}H_{41}$, $CH_3OCH_2$, $CH_3OCH_2CH_2$, $CH_3CH_2OCH_2CH_2OCH_2CH_2$, or $CH_3CH_2OCH_2CH_2OCH_2CH_2OCH_2CH_2$; and a solvent (e.g., water, ethanol, DMSO, and a phosphate buffer solution).

The nucleic acid can be selected from the group consisting of DNA, RNA, and miRNA.

In one aspect, the concentration of the nucleic acid in the solution is about 10-25 ng/μl. In another aspect, the concentration of the nucleic acid in the solution is about 18 ng/μl. However, any suitable concentration of nucleic acid can be used as needed for a particular use (e.g., diagnostic test, sample preservation, etc.).

In aspects described herein, the structure of nucleic acid is stabilized for at least about thirty days to two years. The term "structure of nucleic acid" refers to the native structure of the nucleic acid molecule or initial structure for a non-naturally occurring nucleic acid.

In another aspect, the degradation (DR) ratio of the nucleic acid is from at least about 1 for at least about 30 days to about 5 years. The DR refers to the ratio of intact to degraded nucleic acid molecules in a sample. As described herein, DR is an indicator of the structural stability of nucleic acid in a sample. The term "about 1" can refer to near or close to 1 (e.g., 0.7, 0.8, 0.9, 1.1, 1.2, 1.3, 1.4, or 1.5). As used herein, the term "stable" nucleic acid refers to nucleic acid having a DR of about 1. "Stabilizing" nucleic acid refers to storing nucleic in manner to maintain its structural stability for an extended period of time (e.g., at least about 30 days to about 5 years).

The degradation ratio for a sample nucleic acid can be measured, for example, in accordance with standard forensic methodology. See, e.g., California Department of Justice, Bureau of Forensic Services, DNA Casework Technical Procedures Volume 1, DNA Casework Technical Procedures, epic.org/state-policy/foia/dna-software/7-DNA-Casework-Technical-Procedures-Rev-20-093015.pdf. In one example, the Quantifiler Trio DNA Quantification Kit from ThermoFisher Scientific can be used to measure the degradation ratio. See, www.thermofisher.com/order/catalog/product/4482910. qPCR targets used are summarized in the table below reproduced from the DNA Casework Technical Procedures manual based on the Quantifiler Trio DNA Quantification Kit user manual:

| qPCR Target | Amplicon Length | Copy Number | TaqMan 5'-Dye & 3'-Quencher* |
|---|---|---|---|
| T.Small (human autosomal) | 80 bases | multicopy | VIC & MGB/NFQ |
| T.Large (human autosomal) | 214 bases | multicopy | ABY & QSY |
| T.Y (human male-Y-chromosomal) | 75 bases | multicopy | FAM & MGB/NFQ |
| Internal PCR Control (IPC) | 130 bases | synthetic template | JUN & QSY |

Table reproduced from the Trio User Guide.
*For TaqMan detection, the Trio kit either uses a minor-groove binding/non-fluorescent quencher (MGB/NFQ) system at the 3' end of the probe or a 3'-QSY non-fluorescent quencher.

In another example, the degradation ratio can be quantified by measuring the length of two human nuclear target sequences (e.g., one target that is ~170-190 basepairs (bp) in length and the other 67 bp in length). An internal positive control (IPC) assay is also performed. By comparing quantifications from the two differently sized nuclear target sequences, the assay effectively estimates the extent of DNA degradation in a sample. See, Timken et al., *Quantitation of DNA for Forensic DNA Typing by qPCR*, California Department of Justice Jan Bashinski DNA Laboratory (June 2005) (www.ncjrs.gov/pdffiles1/nij/grants/210302.pdf).

In another aspect, a polymerase chain reaction (PCR) can be performed on the nucleic acid to amplify substantially intact nucleic acid molecules in the solution. For example, PCR can be performed on nucleic acid stored in the solution stored at ambient temperature for at least about 30, 40, 50, 60, 120, 240, 360 days or more after the nucleic acid is added to the solution. Real-time PCR can be used to measure the DR of a nucleic acid stored in an APS and indicate the stabilizing effects of the APS.

In another aspect, the solution is maintained at ambient temperature. The term "ambient temperature" refers to room temperature, or the temperature at which human or animal habitation or commercial facilities is maintained. In one aspect, ambient temperature can be from about 20 to 30 degrees centigrade.

Further aspects provide a kit comprising a compound selected from the group consisting of:

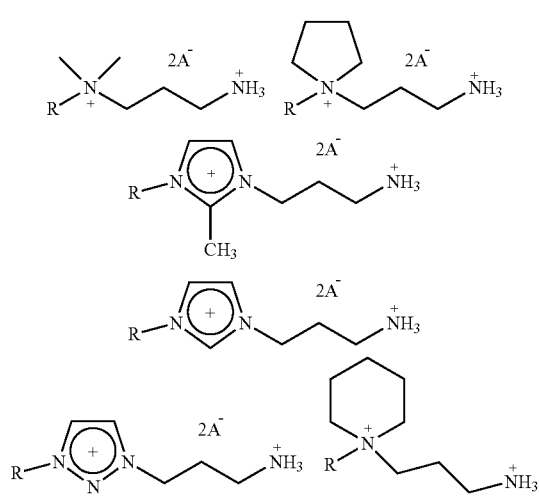

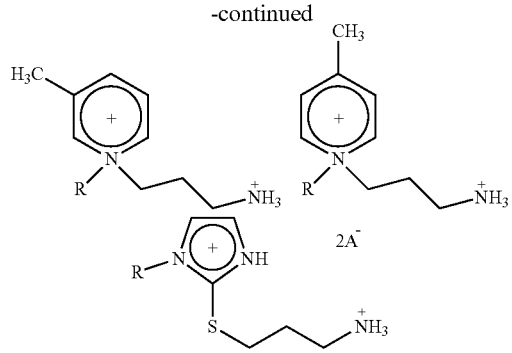

wherein X is N, O, or S; A is Cl, Br, I, OTf, $NTf_2$, $BF_4$, $PF_6$, OAc, $N(CN)_2$, $MeSO_3$, $H_2PO_3$, dialkylphosphate, SCN, citrate, docusate, bis(oxylate)borate, oxalate, alaninate, or serinate; R is $CH_3$—$C_{16}H_{37}$, $CH_3$—$C_{16}H_{37}$, $CH_3$—$C_{16}H_{37}$, pyroether groups, C—O—C, $CH_3$—$C_{20}H_{41}$, $CH_3OCH_2$, $CH_3OCH_2CH_2$, $CH_3CH_2OCH_2CH_2OCH_2CH_2$, or $CH_3CH_2OCH_2CH_2OCH_2CH_2OCH_2CH_2$; and a solvent (e.g., water, ethanol, DMSO, and a phosphate buffer solution).

In this aspect, the kit can include commercial packaging and labelling, including instructions for use, individual containers for compounds described herein, one or more suitable solvents as described herein, and additional reagents or containers as needed. The kit can be portable and include devices or an apparatus to aid in collection and storage of one or more samples and samples stored in the solution which includes the compounds described herein. A kit suitable for use in the field, at home, or in a laboratory setting can be provided.

Further aspects provide methods of amplifying nucleic acid by obtaining a nucleic acid mixture sample; dissolving the nucleic acid mixture sample in the compounds described herein and a solvent; and amplifying nucleic acid from the nucleic acid mixture using one or more nucleic acid probes wherein the DR of the nucleic acid mixture sample is at least about 1 for at least about 30 days.

The term "amplifying nucleic acid" refers to a process by which a nucleic acid or other probe can be used to bind to a desired region of a nucleic acid (e.g., a gene, promoter region, non-coding region) and undergo an amplification process by which the nucleic acid is copied to produce enough nucleic acid for detection by agarose gel electrophoresis or another method. The polymerase chain reaction is one method of amplifying nucleic acid. In addition, UV-vis spectroscopy investigation can provide qualitative information on the stability of DNA conformation, and circular dichroism spectroscopy (CD) is considered as a most suitable tool to have conformational information on DNA, although this also provides qualitative information as well.

Figure 3:
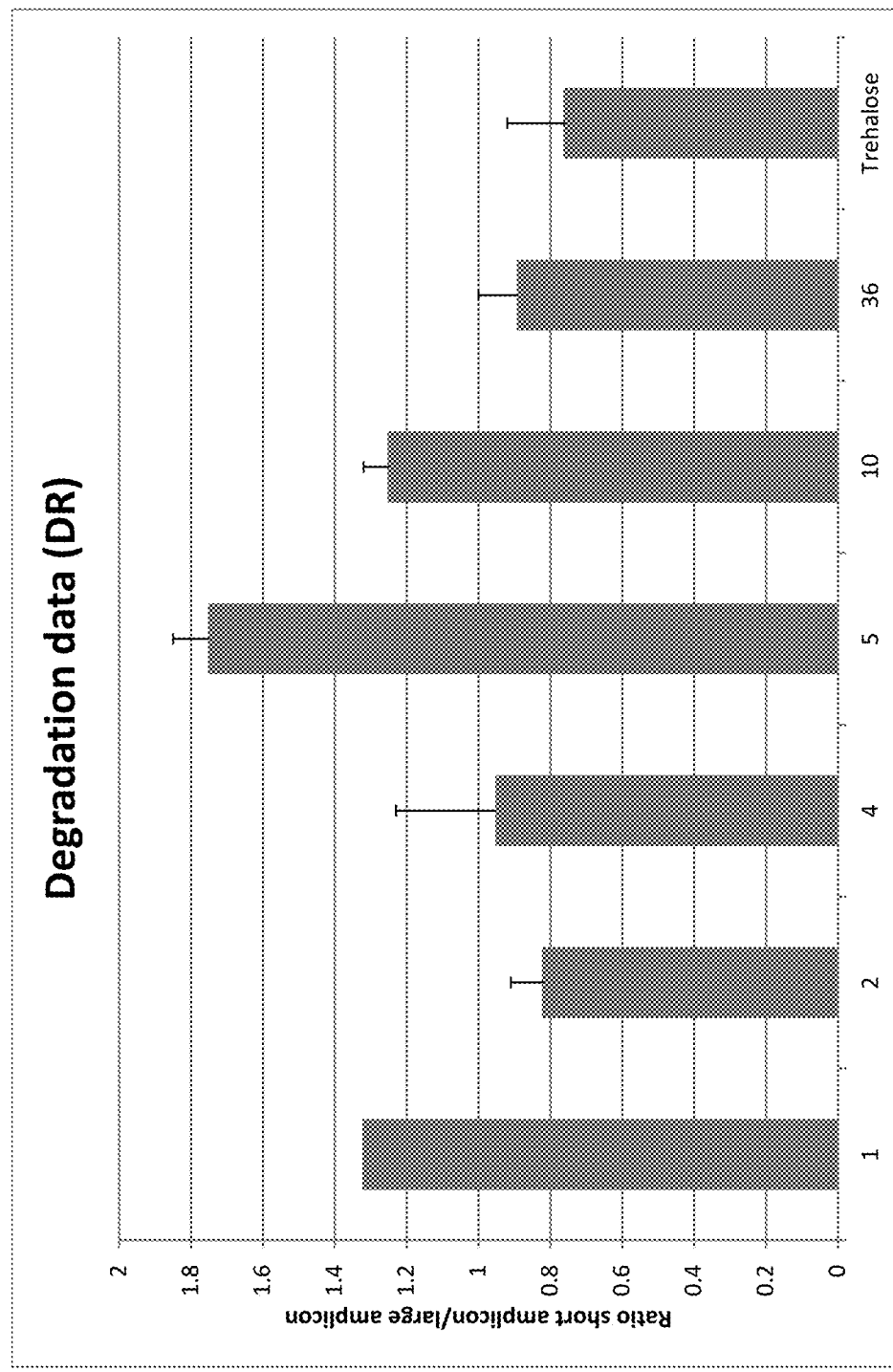
FIG. 3 provides exemplary degradation ratios (DR) of nucleic acids after use of selected APSs measured by real-time PCR, as described herein.

As shown in Table 1 and FIG. 3, human DNA molecules were found to be soluble in the APSs and exhibit long-term stability at ambient temperatures and in liquid from (no drying needed). DNA stored is the APSs described herein have been shown to be stable for at least two years at ambient temperature (Table 1 and FIG. 3). The DR of APSs is an indication of the degree of DNA degradation since a degraded sample will contain a higher concentration of intact amplifiable small target sequence than the larger target sequence.

In one aspect, as shown in Table 1, compounds 4, 10, and 36 have DR values closest to 1 (i.e., 0.9545, 0.89, and 1.25).

However, the remaining compounds impart stability to nucleic acid molecules. FIG. 3 provides a graphical representation of the data of Table 1 with the compound numbers shown on the x-axis.

In one aspect, the DR is calculated as: DR=(Small target/ Large target). Ideally for non-degraded DNA, the DR is about 1 and increases with extent of degradation. Trehalose was used as a standard to compare the stability of DNA in standard solution to the stability of DNA in APSs (FIG. 3).

The present data show exemplary preparation of APSs with linked cations in which one charge center is protic (i.e., contains exchangeable $H^+$) and the other is aprotic (i.e., the positive charge is generally durable, and the cation is not in equilibrium with neutral components). Novel APSs were formed as white crystalline solid in quantitative yields and structural purity was determined by $^1H$ and $^{13}C$ NMR spectroscopy (see, e.g., FIGS. 4-8 for the $^1H$ and $^{13}C$ NMR spectra of representative APSs).

Figure 4A:
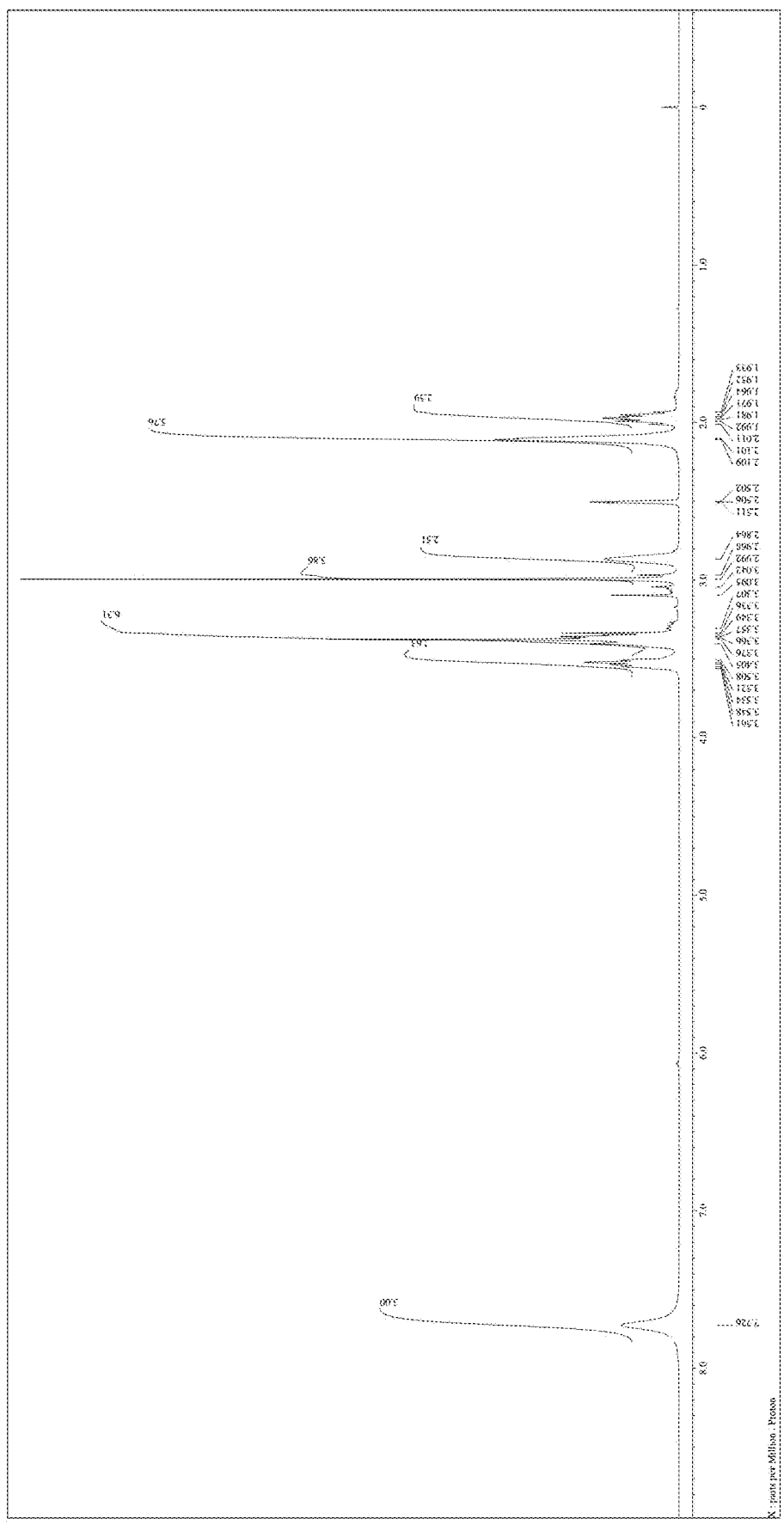
FIGS. 4A and 4B provide exemplary $^1$H and $^{13}$C NMR spectra of APS 1.
Figure 4B:
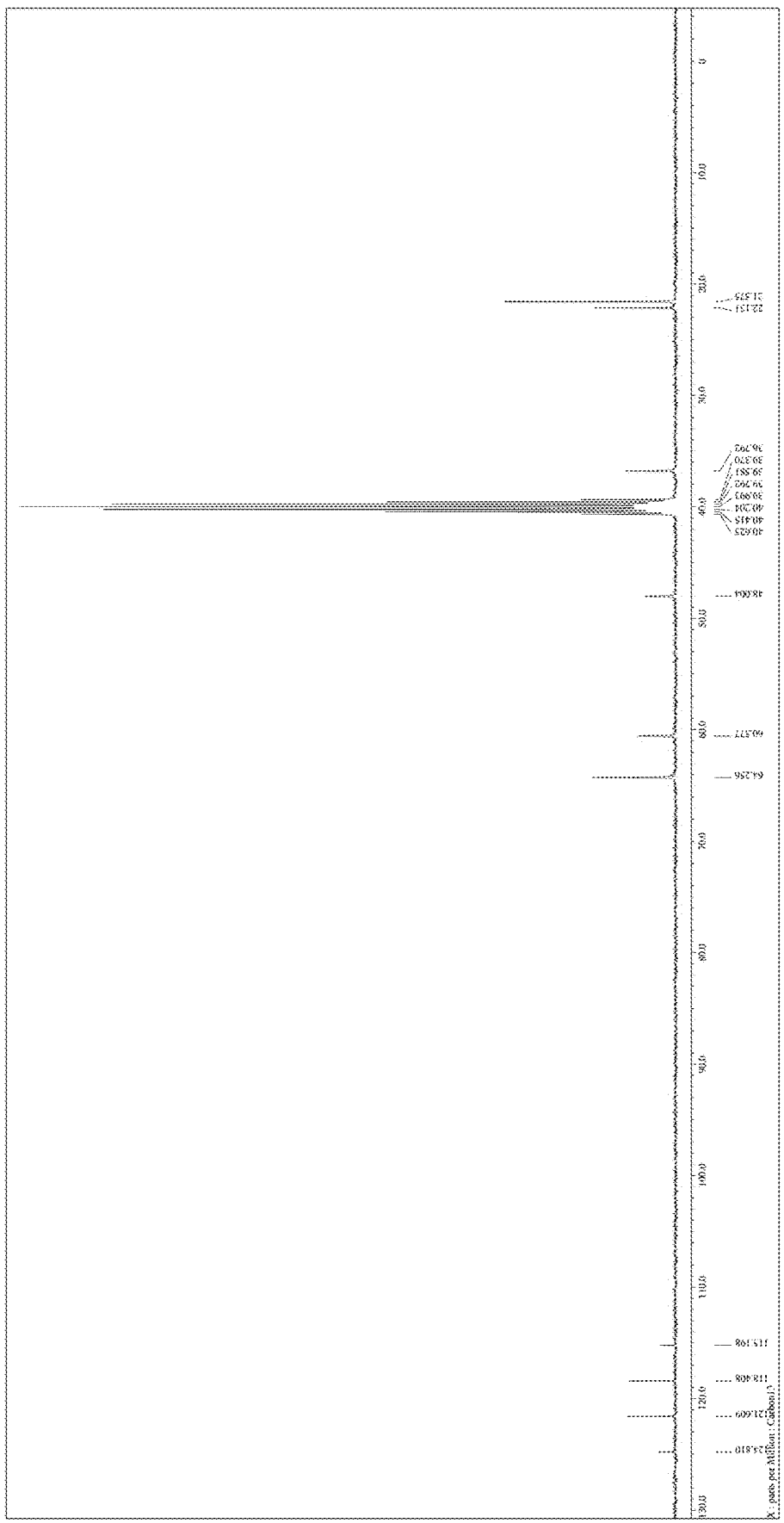
Figure 5A:
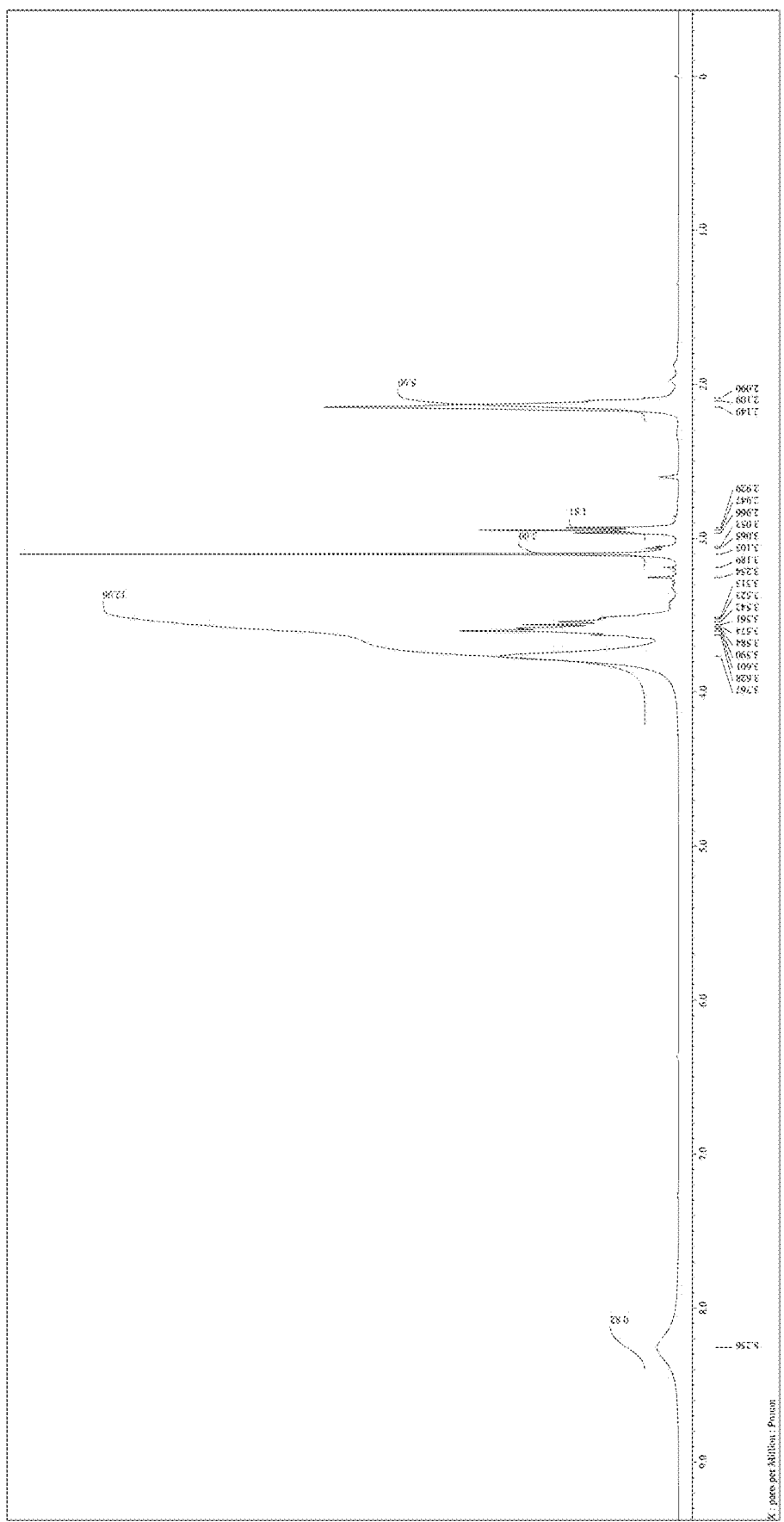
FIGS. 5A and 5B provide exemplary $^1$H and $^{13}$C NMR spectra of APS 2.
Figure 5B:
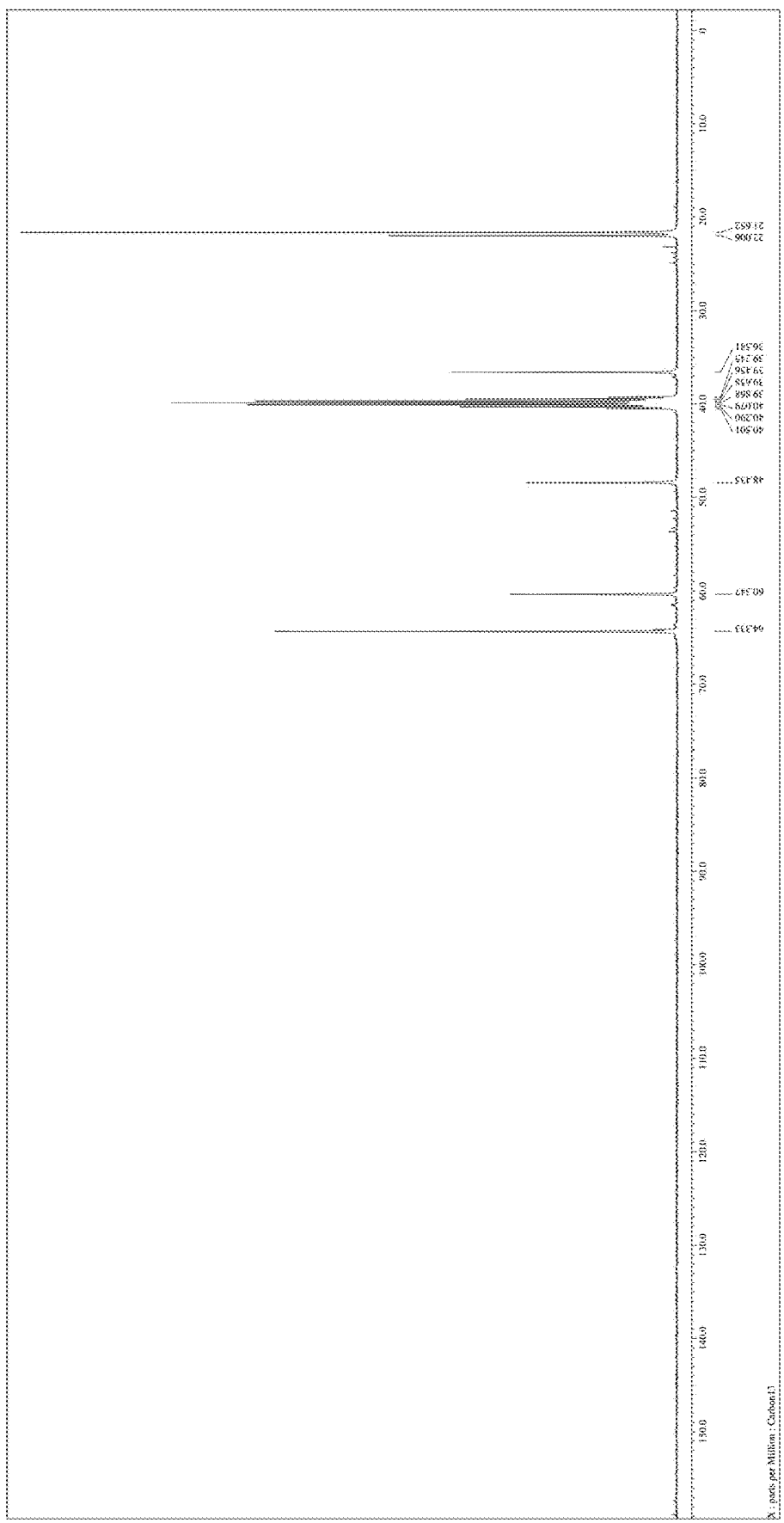
Figure 6A:
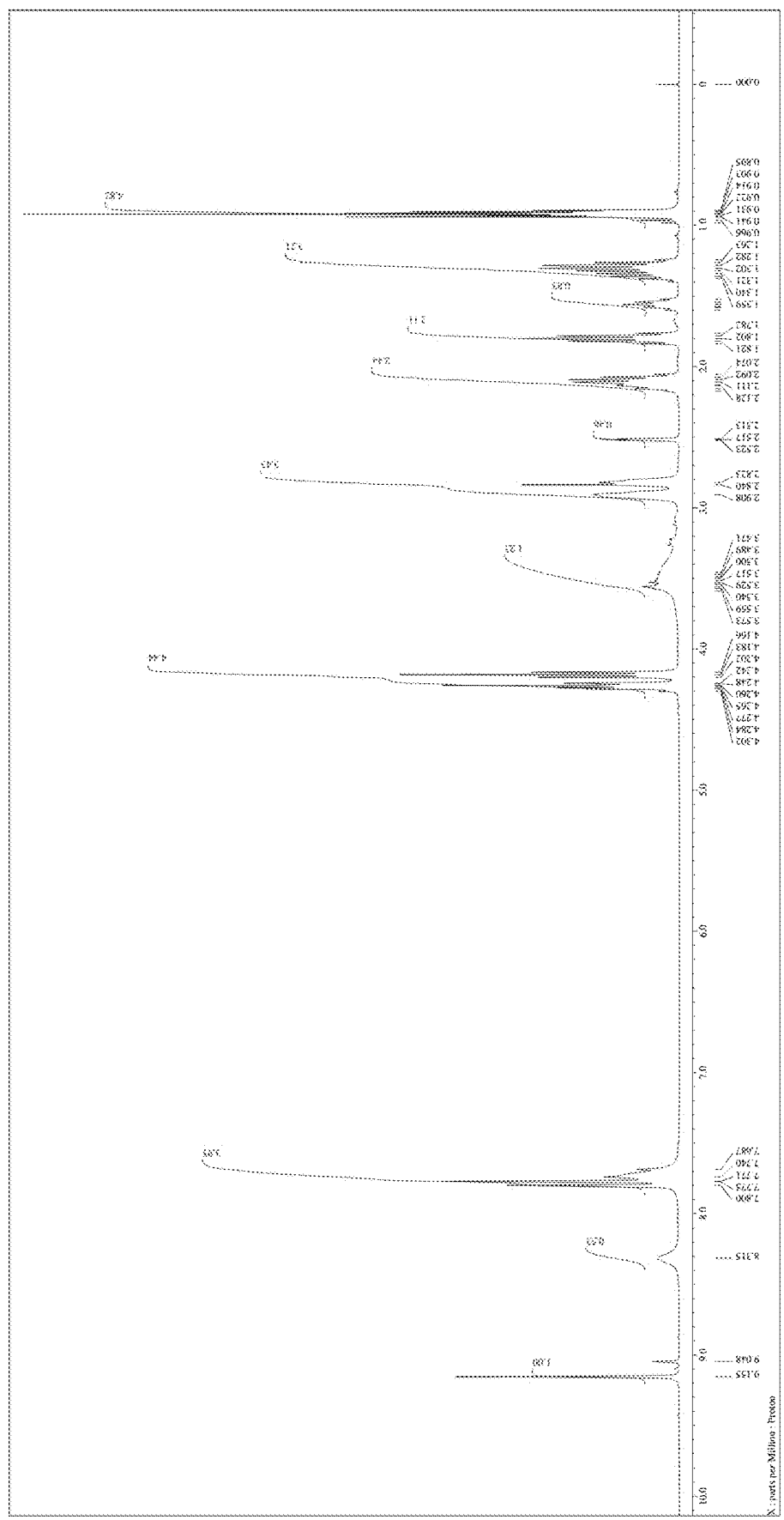
FIGS. 6A and 6B provide exemplary $^1$H and $^{13}$C NMR spectra of APS 4.
Figure 6B:
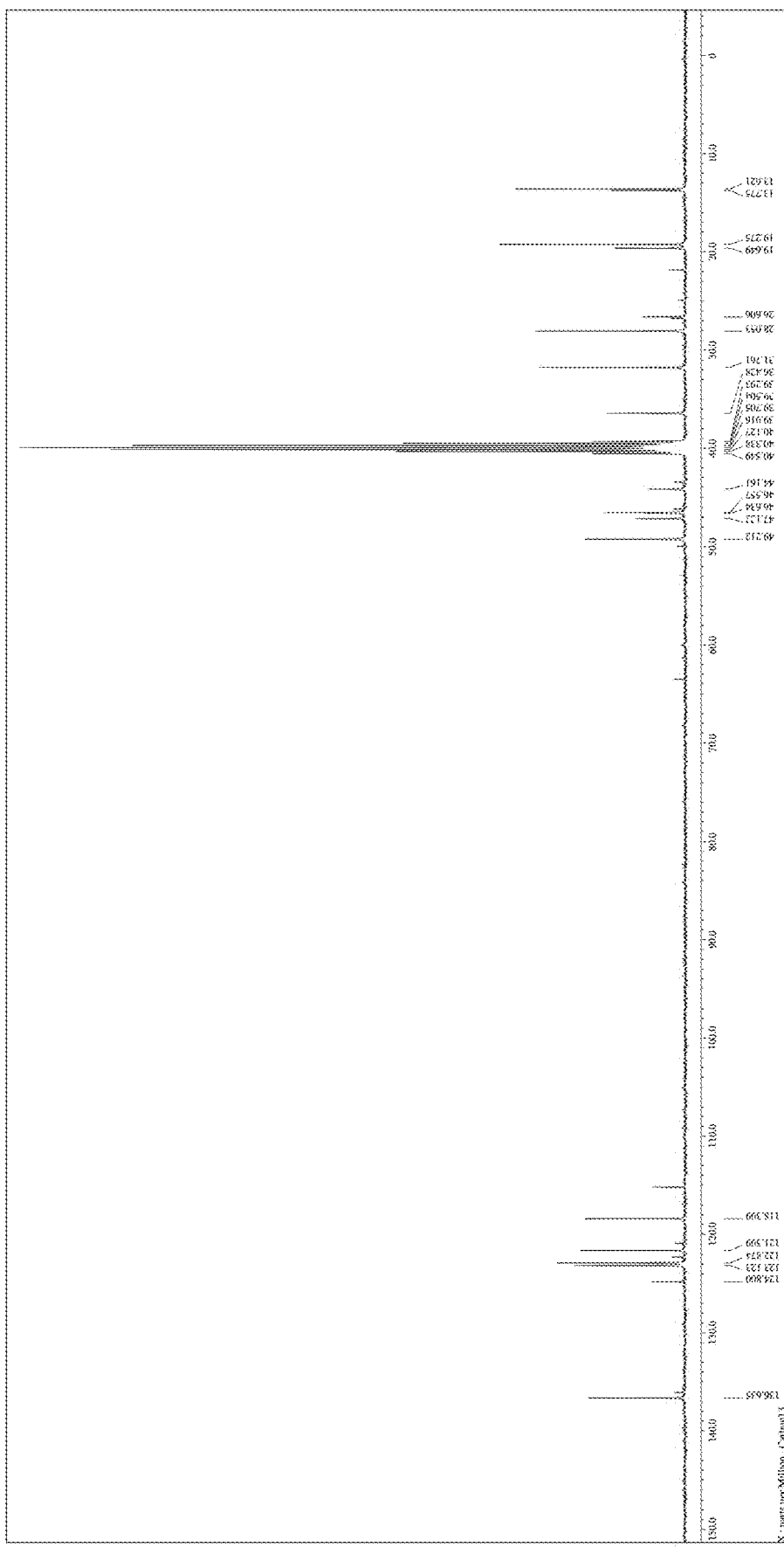
Figure 7A:
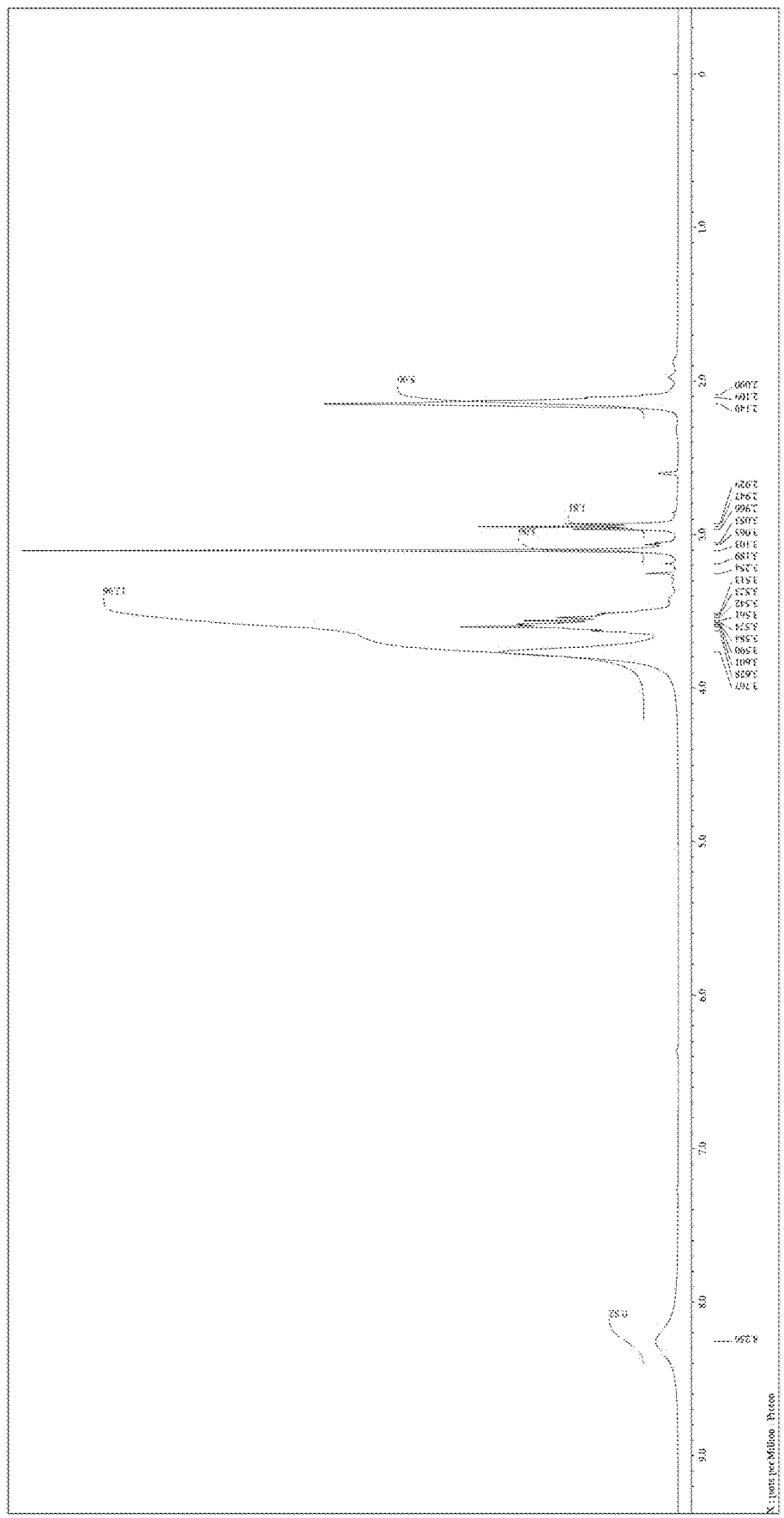
FIGS. 7A and 7B provide exemplary $^1$H and $^{13}$C NMR spectra of APS 5.
Figure 7B:
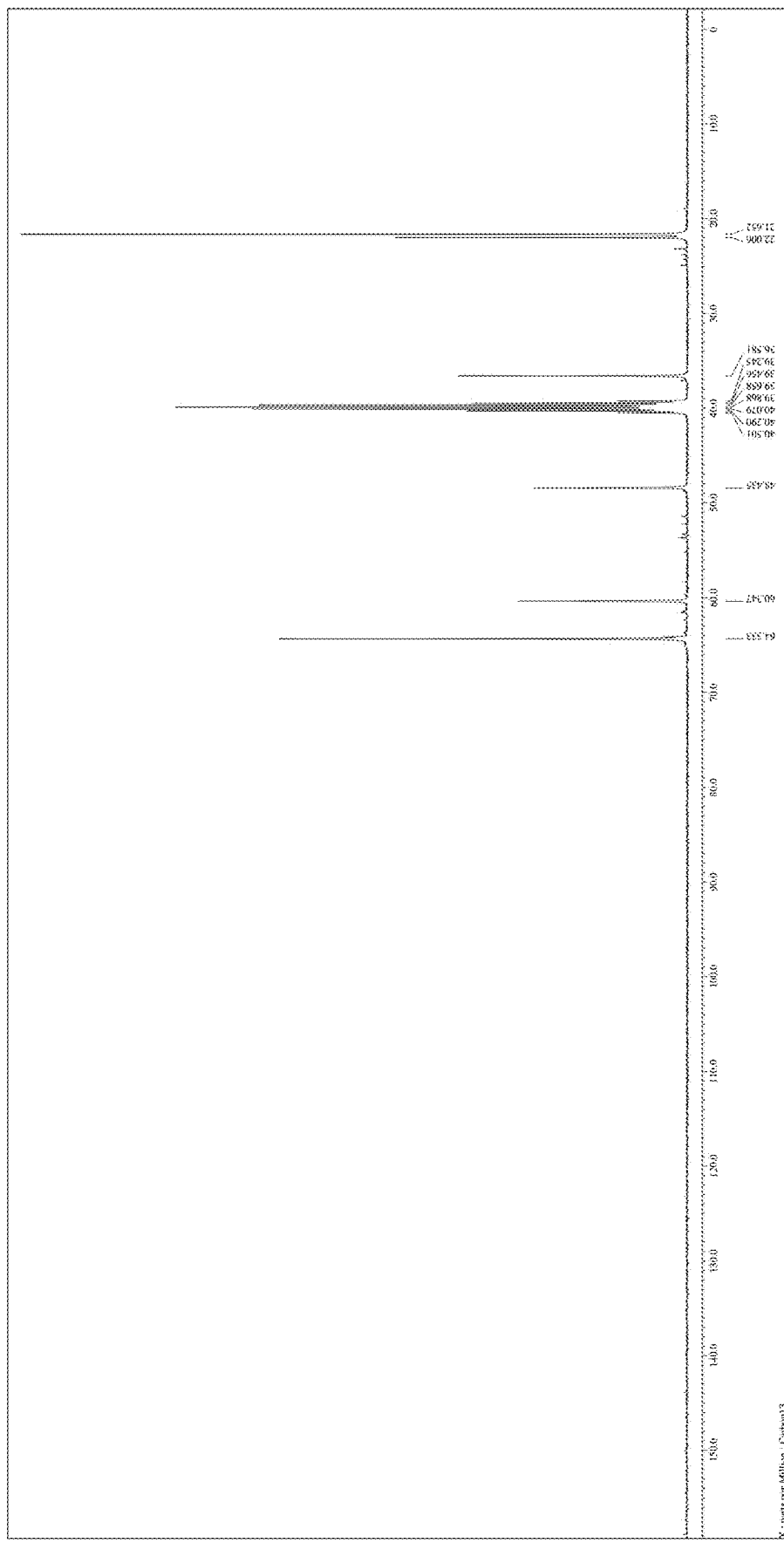
Figure 8A:
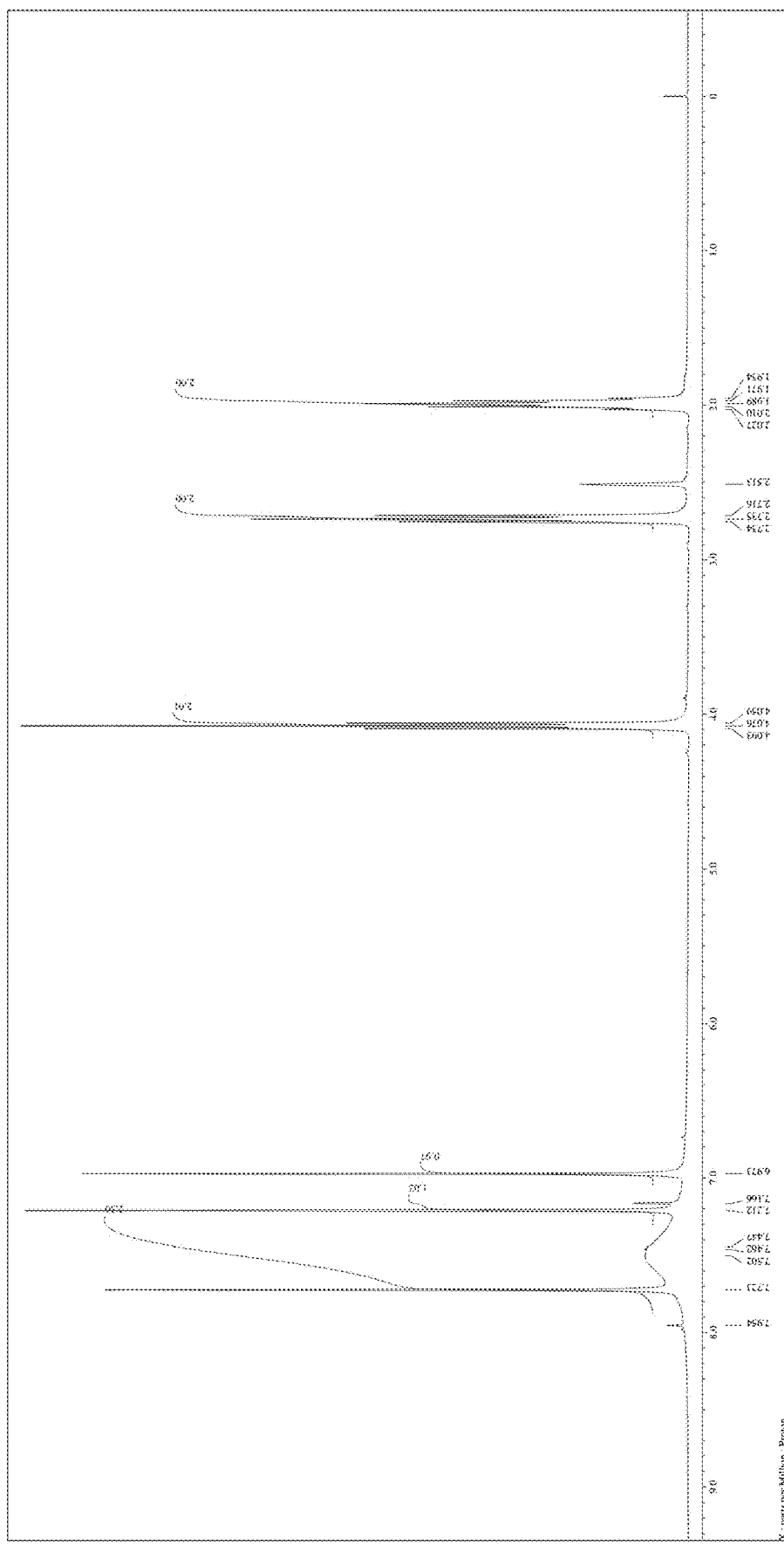
FIGS. 8A and 8B provide exemplary $^1$H and $^{13}$C NMR spectra of APS 10.
Figure 8B:
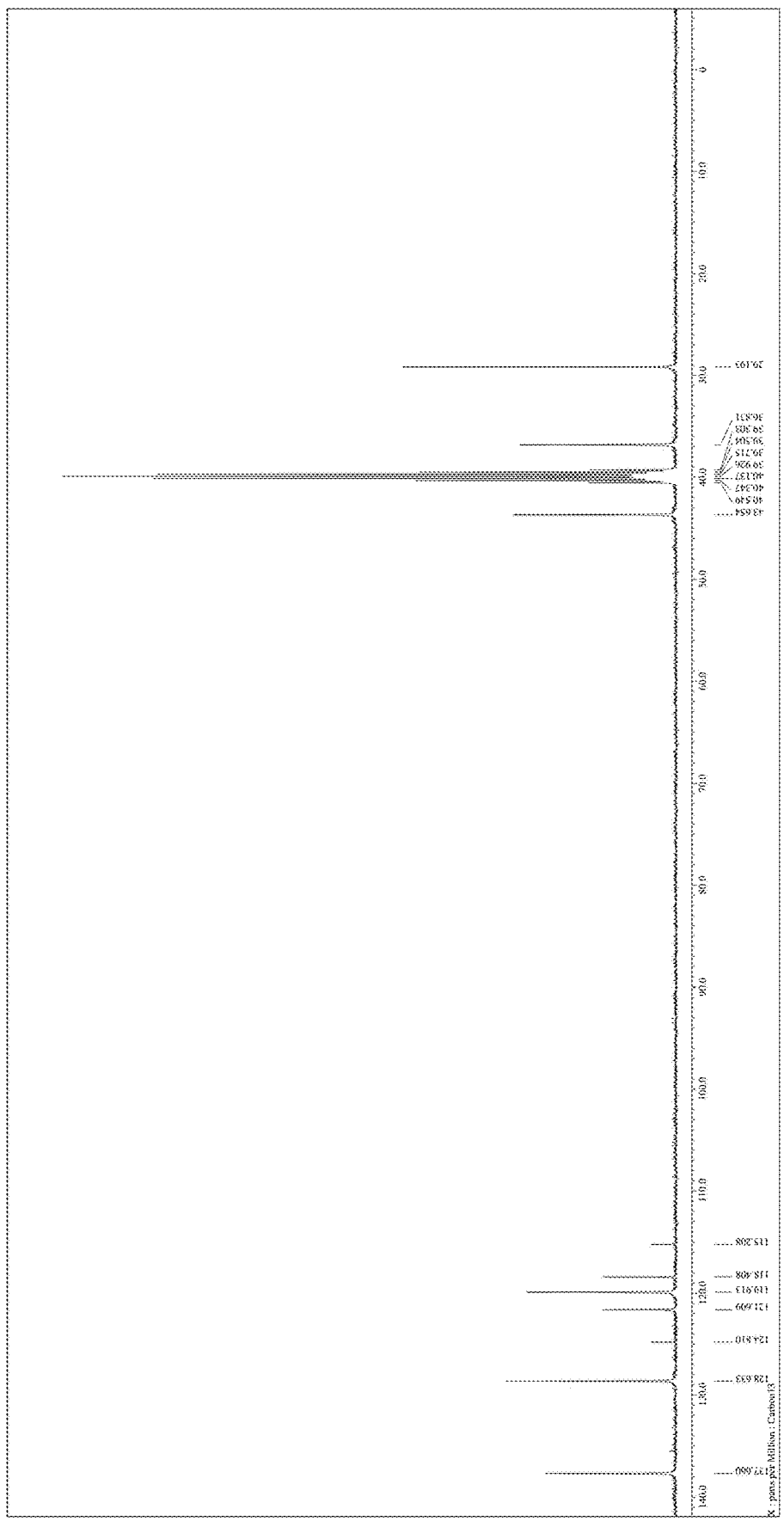

FIGS. 4A and 4B provide an exemplary $^1H$ and $^{13}C$ NMR spectra of APS 1. FIGS. 5A and 5B provide an exemplary $^1H$ and $^{13}C$ NMR spectra of APS 2. FIGS. 6A and 6B provide exemplary $^1H$ and $^{13}C$ NMR spectra of APS 4. FIGS. 7A and 7B provide an exemplary $^1H$ and $^{13}C$ NMR spectra of APS 5. FIGS. 8A and 8B provide an exemplary $^1H$ and $^{13}C$ NMR spectra of APS 10. The APS number corresponding to the analyzed APS is provided in Table 1. The spectra confirm the structural identification of the APS products Aspects described herein comprise variants of APSs. For example, structural variability for APSs can be achieved by varying aprotic head groups (e.g., quaternary ammonium, pyrrolidinium, methimazolium, pyridinium, 1,2,3-triazolium and imidazolium). In another aspect, aprotic sites in the APS structures provide a locus of cationic charge and form the electrostatic binding with nucleic acids as anionic biopolymers.

In yet another aspect, a linker consists of, for example, a three-carbon non-polar chain can be used to bridges the aprotic sites and the protic ($NH_3^+$) domains. In order to fit the APSs into the DNA's grooves, the cationic aprotic sites and the protic moiety are can be connected through, for example, three or more carbons. Increasing the length of the linker can be used to modify the activity of APSs. Thus, the length of a linker can be used to alter the activity of APSs.

The cations of APSs can be paired with a variety of hydrophilic (kosmotropic) anions. Without being bound by theory, it is believed that the unique molecular structures of the APSs governs the DNA complexation for long-term storage.

Aromatic heterocycles (e.g. imidazolium) in APSs exhibit well-balanced polar domains for packaging of nucleic acids, which can facilitate DNA preservation. Without being bound by theory, it is believed that the positive charge delocalization throughout the heterocyclic moiety leads to increased hydrophobicity in the polar head, which generates improved packing parameters, enabling the formation of well-packed lamellar structures that improve the stability of DNA. Further, it is believed that the APS ions disrupt the water cage around DNA leading to partial dehydration of the DNA molecules, preventing hydrolysis of DNA over extended periods of time.

In addition to the contribution of cations, anions impact DNA stability. The variability of DNA stability is believed to be attributed to the higher kosmotropicity of $[Cl]^-$ anion (Table 1, APS 2) in comparison to $[NTf_2]^-$ anion (Table 1, APS 1). For example, the chaotropic anion ($[NTf_2^-]$), with two cationic centers, imparts less stability to DNA than use of a kosmotropic anion ($[Cl^-]$).

APSs as described herein form robust hydrogen bonding networks while protic salts-like volatility is substantially suppressed. Without being bound by theory, it is believed that the stability of the DNA double helix in these salts depends on a balance of interactions including: a) hydrogen bonding between DNA ribose sugar, bases (A and T) and the protic site of APSs; b) pi-pi interaction between the bases and the aromatic APSs; and c) electrostatic interactions between negatively-charged phospholipids in the DNA backbone and aprotic site of APSs.

In another aspect, it is believed that the groove-binding mechanism of APS cations contributes dramatically to DNA stability via forming a strong hydrogen bonding network, in addition to their electrostatic associated with the DNA backbone. Due to the presence of two cationic sites in the APS structures—aprotic (heterocyclic rings) and protic ($^+NH_3$)—aprotic head groups accumulate around the negatively-charged phosphate groups of DNA and protic sites of the APSs forming hydrogen bonds with ribose sugars and bases.

In addition, the high density of APS cations in the DNA solvation shell screens the interisland phosphate repulsions. It is believed that the partial dehydration of DNA by APSs prevents the hydrolytic reactions that denature DNA. The strong APS cations—DNA interactions can prevent intermolecular interactions between the neighboring DNA strands, a phenomenon known to be associated with the B to A conformational transition (Chandran et al., 2012).

Previously, it was shown by MD simulations and NMR spectroscopy that the choline cation ($[Me_3NCH_2CH_2OH]^+$) fits well into the minor groove of the A-T base pairs in DNA duplex, allowing the formation of multiple hydrogen bonds between cations and DNA atoms (Nakano et al., 2014). It is believed that the unique conjugative interactions (hydrogen bonds, electrostatic and pi-pi) between the APSs and DNA molecules enable enhanced stability of the DNA duplex in the sequence-specific manners. It is believed that the dications bind primarily to nucleotide phosphates and stabilize the order of DNA structures by reducing repulsion between phosphate groups and permit the dications to accumulate in DNA grooves. It is also believed that, due to strong hydrogen bonding between protic sites of the APSs and DNA backbone, APSs/do not go through the exchange process.

In addition, the data described herein (e.g., FIG. 3) show that protected DNA in APSs was compatible with downstream applications, i.e., PCR, real-time PCR and sequencing) with up to about 2 years (to date) of genomic DNA stability of DNA stored in APSs at room temperature based on PCR studies. APSs provide a reliable and facile alternative to cold and dry storage for long-term biobanking of valuable DNA samples without the costs and risks associated with cold/dry chain shipping and storage.

APS use can be expanded to applications where long-term biomolecule storage at ambient temperatures is advantageous (e.g., applications where very high hydrogen bonding capacities as well as dynamic acid-base behaviors are sought). Examples include, but are not limited to, RNA, protein and enzyme stabilization, degradation prevention, and storage. Furthermore, extended stability of DNA in these APSs can be used in advanced nanomaterials (e.g., biocircuits, biodevices and biosensors). The APSs have been described in accordance with several examples, which are intended to be illustrative in all aspects rather than restrictive. Thus, the aspects described herein can be varied in synthesis and use, as ascertained herein by a person of ordinary skill in the art.

EXAMPLE

Experimental Methods
Representative Synthetic Procedure

The synthetic approach used to prepare the APSs reported in this paper from Mirjafari et al., (Mirjafari et al., 2013).

One equiv. of 3-(dimethylamino)-1-propylamine was added into a pre-dried round bottomed flask, to which was then added reagent-grade methanol to completely dissolve it. The flask was charged with an egg-shaped magnetic stir bar and immersed in an ice-water bath. One equiv. of di-tert-butoxycarbonyl anhydride was weighed out into a beaker and added, in portions, to the stirred original solution. Upon addition, $CO_2$ is released. di-tert-butoxycarbonyl anhydride was added slowly to the amine solution to prevent the effervescing liquid from overflowing the flask. Once this addition was complete, stirring continued overnight in open flask at room temperature. Afterwards, volatiles (methanol and tert-butyl alcohol) were removed in vacuo on a rotary evaporator while heating with a water bath at ca. 80° C. The product was then dissolved in of reagent grade acetonitrile, to which was then added one molar equivalent (38.6 g) of n-butyl iodide. The flask was stoppered, and the reaction mixture stirred for 24 hours. Afterwards, the volatiles were removed again using a rotary evaporator in combination with a hot water bath. Having confirmed the completeness of the alkylation reaction via $^1$H NMR, the residue was then dissolved in 2.0M hydrochloric acid (HCl) and stirred. After stirring overnight, volatiles were removed by rotary evaporation (with heating to 100° C.) and NMR is used to check for completeness of de-protection, as any remaining protected material will be essentially impossible to remove from the final product.

While the aspects described herein have been disclosed with reference to certain embodiments, numerous modifications, alterations, and changes to the described embodiments are possible without departing from the sphere and scope of the present invention, as defined in the appended claims. Accordingly, it is intended that the present disclosure not be limited to the described aspects, but that it has the full scope defined by the language of the following claims, and equivalents thereof.

REFERENCES

Baust, J. G, Strategies for the Storage of DNA. Biopreserv. Biobank., 2008, 6, 251-252.
Bonnet, J.; Colotte, M.; Coudy, D.; Couallier, V.; Portier, J.; Morin, B.; Tuffet, S. Chain and conformation stability of solid-state DNA: implications for room temperature storage. Nucleic Acids Res. 2010, 38, 1531-1546.
Brandt, A.; Gräsvik, Hallett, J. P.; Welton, T. Deconstruction of lignocellulosic biomass with ionic liquids. Green Chem. 2013, 15, 550-583.
Chandran, A.; Ghoshdastidar, D., Senapati, S. Groove binding mechanism of ionic liquids: a key factor in long-term stability of DNA in hydrated ionic liquids? J. Am. Chem. Soc. 2012, 134, 20330-20339.
Hammouda, B., Worcester, D. The denaturation transition of DNA in mixed solvents. Biophys. J. 2006, 91, 2237-2242.
Jobling, M. A.; Gill, P. Encoded evidence: DNA in forensic analysis. Nat. Rev. Genet. 2004, 5, 739-751.
Kutzler, M. A.; Weiner, D. B. DNA vaccines: ready for prime time? Nat. Rev. Genet. 2008, 9, 776-788.
Legoff, J; Tanton, C.; Lecerf, M.; Gresenguet, G.; Nzambi, K.; Bouhlal, H.; Weiss, H.; Belec, L. Influence of storage temperature on the stability of HIV-1 RNA and HSV-2 DNA in cervicovaginal secretions collected by vaginal washing. J. Virol. Methods 2006, 138, 196-200.
Lukin, M.; de los Santos, C. NMR Structures of Damaged DNA. Chem. Rev., 2006, 106, 607-686.
Shamashina, J. L.; Berton, P.; Rogers, R. D. Advances in functional chitin materials: A review. ACS Sustainable Chem. Eng. 2019, 7, 6444-6457.
Singh, N.; Sharma, M.; Mondal, D.; Pereira, M. M.; Prasad, K. Very high concentration solubility and long-term stability of DNA in an ammonium-based ionic liquid: a suitable medium for nucleic acid packaging and preservation. ACS Sustainable Chem. Eng. 2017, 5, 1998-2005.
Mirjafari, A.; Mobarrez, N.; Pham, L. N.; Sykora, R. E.; West, K. N.; Davis, Jr., J. H. Building a bridge between aprotic and protic ionic liquids. RSC. Adv., 2013, 3, 337-340.
Nakano, M.; Tateishi-Karimata, H.; Tanaka, S.; Sugimoto, N. Choline ion interactions with DNA atoms explain unique stabilization of A-T base pairs in DNA duplexes. A microscopic view. J. Phys. Chem. B, 2014, 118, 379-389.
Reilly, J. T.; Coats, M. A.; Reardon, M. M.; Mirjafari, A. Study of biocatalytic activity of histidine ammonia lyase in protic ionic liquids. J. Mol. Liq. 2017, 248, 830-832.
Vijayaraghavan, R.; Izgorodin, A.; Ganesh, V.; Surianarayanan, M.; MacFarlane, D. R. Long-term structural and chemical stability of DNA in hydrated ionic liquids. Angew. Chem., Int. Ed. 2010, 49, 1631-1633.

What is claimed is:

1. An aprotic-protic ionic salt composition comprising a compound selected from the group consisting of:

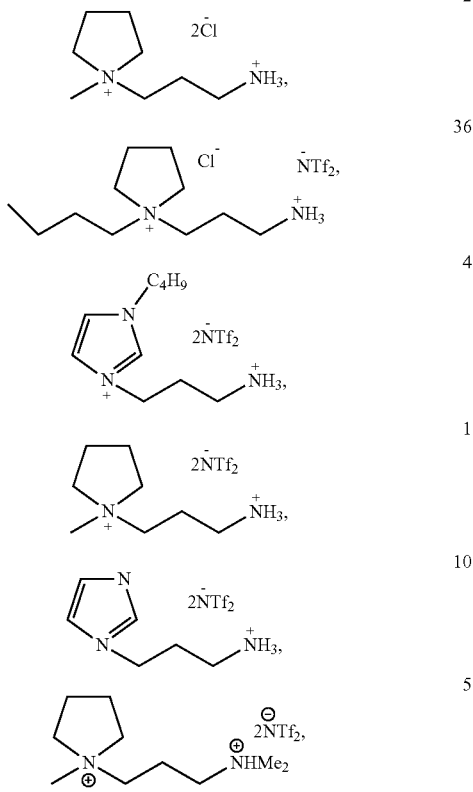

-continued
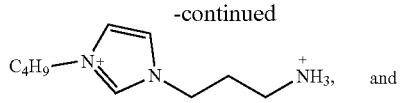
and
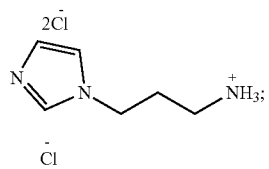
a solvent; and a nucleic acid mixture.
2. The composition of claim 1, wherein the solvent is selected from the group consisting of water, ethanol, DMSO, and a phosphate buffer solution.
3. The composition of claim 1, wherein the nucleic acid is selected from the group consisting of DNA, RNA, and miRNA.
4. The composition of claim 1, wherein the compound is
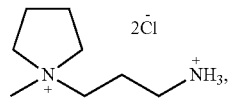
2
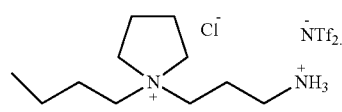
36
\* \* \* \* \*